United States Patent [19]

Shepard et al.

[11] 4,256,889

[45] Mar. 17, 1981

[54] PROCESS FOR THE PREPARATION OF IMINO-BRIDGED BENZOCYCLOHEPTAPYRIDINES

[75] Inventors: Kenneth L. Shepard, Ambler, Pa.; Daniel G. Brenner, Medford, Mass.

[73] Assignee: Merck & Co., Inc., Rahway, N.J.

[21] Appl. No.: 93,410

[22] Filed: Nov. 13, 1979

Related U.S. Application Data

[63] Continuation-in-part of Ser. No. 959,049, Nov. 9, 1978, abandoned.

[51] Int. Cl.$^3$ .......................................... C07D 471/18
[52] U.S. Cl. .................................. 546/63; 424/256; 542/429; 542/455; 546/93
[58] Field of Search .......................................... 546/63

[56] References Cited

U.S. PATENT DOCUMENTS

| 3,892,756 | 7/1975 | Nedelec et al. | 546/72 |
| 4,052,508 | 10/1977 | Anderson et al. | 546/101 |
| 4,064,139 | 12/1977 | Anderson et al. | 260/313.1 |
| 4,123,546 | 10/1978 | Haire | 424/274 |

OTHER PUBLICATIONS

Patai, S., *The Chemistry of the Carbon—Nitrogen Double Bond,* Interscience, London, 1970, pp. 67–68.
March, J., *Advanced Organic Chemistry,* McGraw Hill, New York, 1968, pp. 689–690 and pp. 331–332.
Villani, F., et al., *J. Het. Chem.,* 9, 1203–1207 (1972).
Villani, F., et al., *J. Het. Chem.,* 8, 73–81 (1971).

*Primary Examiner*—Henry R. Jiles
*Assistant Examiner*—Richard A. Schwartz
*Attorney, Agent, or Firm*—Mario A. Monaco; William H. Nicholson

[57] ABSTRACT

Benzocycloheptapyridines with an imine bridge in the cycloheptane ring, derivatives and pharmaceutically acceptable salts thereof are useful as anxiolytics, antidepressants, anticonvulsants, muscle relaxants and in the treatment of mixed anxiety-depression, minimal brain dysfunction and extrapyramidal disorders such as Parkinson's disease. They are prepared, for example, by treatment of a benzo[5,6]cyclohepta[1,2-c]pyridin-11-one with ammonia to give the 11-imine, acylation of the imine, treatment of the protected imine with an alkyllithium to provide the 11-alkyl-11-acylamino compound, treatment with acid or base to cause ring closure to an 11-alkyl-6,11-acylimino compound followed by removal of the protecting group, either hydrolytically or hydrogenolytically.

4 Claims, No Drawings

PROCESS FOR THE PREPARATION OF IMINO-BRIDGED BENZOCYCLOHEPTAPYRIDINES

BACKGROUND OF THE INVENTION

This is a continuation-in-part of copending application Ser. No. 959,049, filed Nov. 9, 1978, now abandoned.

This invention is concerned with novel benzocycloheptapyridines with an imine bridge in the cycloheptane ring, and a substituent at both bridgehead carbons, derivatives and pharmaceutically acceptable salts thereof which are useful as anxiolytics, antidepressants, anticonvulsants, muscle relaxants and in the treatment of mixed anxiety-depression, minimal brain dysfunction and extrapyramidal disorders such as Parkinson's disease.

They have structure

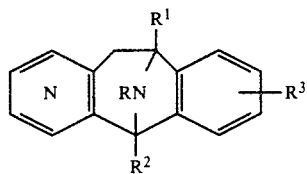

Structurally related compounds are known in the art to have qualitatively similar utilities. For example U.S. Pat. No. 3,892,756 discloses 10,11-dihydro-5H-dibenzo[a,b]cyclohepten-5,10-imine and derivatives, and U.S. Pat. No. 4,064,139 and 4,052,508 disclose 9,10-dihydroanthracen-9,10-imines and pyridine analogs respectively.

The invention is also concerned with a novel process for producing the novel compounds, and other compounds with only one bridgehead substituent such as those described in U.S. Patent Application Ser. No. 074,367, especially wherein $R^1$ is hydrogen. The novel compounds of that Application are so limited because there was no process available for synthesis of the compounds wherein $R^1$ and $R^2$ are both other than hydrogen.

Now with the present invention there is described a novel process for the synthesis of novel compounds wherein $R^1$ and $R^2$ substituents are both other than hydrogen, and of other compounds wherein $R^1$ is hydrogen and $R^2$ is other than hydrogen.

DETAILED DESCRIPTION OF THE INVENTION

The novel compounds of this invention have structural formulae:

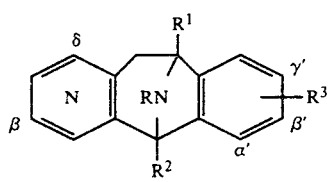

or a pharmaceutically acceptable salt thereof, wherein N is in the $\beta$- or $\delta$-position; $R^1$ and $R^2$ are independently, (1) lower alkyl, especially $C_{1-5}$ alkyl, preferably methyl or ethyl,
(2) lower alkenyl, especially $C_{2-5}$ alkenyl, preferably vinyl or allyl,
(3) phenyl-lower alkyl, especially phenyl $C_{1-3}$ alkyl, preferably benzyl,
(4) lower cycloalkyl, especially $C_{3-6}$ cycloalkyl, preferably cyclopropyl or cyclohexyl,
(5) lower(cycloalkyl-alkyl), especially $C_{3-6}$ cycloalkyl-$C_{1-3}$ alkyl;

R is
(1) hydrogen,
(2) $R^1$, or
(3) di(lower alkyl)amino-lower alkyl, especially di($C_{1-3}$ alkyl)amino-$C_{1-5}$ alkyl; and $R^3$ is
(1) hydrogen,
(2) halogen, such as chloro, bromo, fluoro, or iodo,
(3) lower alkoxy, especially $C_{1-5}$ alkoxy, preferably methoxy,
(4) trifluoromethylthio,
(5) cyano, or
(6) carboxy.

It is preferred that the nitrogen of the pyridine ring be in the $\beta$ or $\delta$ position, and most preferably in the $\beta$-position.

Another preferred group of compounds is that wherein $R^3$ is hydrogen.

Where $R^3$ is other than hydrogen, it is preferred that it occupy the $\beta'$ and/or $\gamma'$ positions of the tricyclic ring system.

Preferred definitions for R, $R^1$ and $R^2$ are independently hydrogen, lower alkyl, especially methyl, or benzyl.

The novel process of this invention is illustrated by the following reaction scheme:

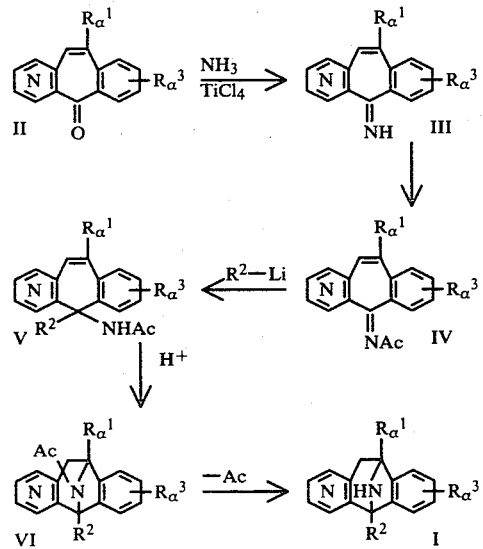

wherein $R_a^1$ is $R^1$ or hydrogen; $R_a^3$ is hydrogen or halo; and Ac is acyl.

The first step in the novel process is formation of the unexpectedly stable imine (III) by treatment of the ketone (II) with gaseous ammonia in the presence of titanium tetrachloride. The reaction is conducted in an inert organic solvent in which the starting materials are soluble, especially an aromatic solvent such as toluene, benzene or the like. The temperature is not critical and may be at about −10° C. to about +50° C. preferably between ice-bath and room temperatures. Times from 2 to about 10 hours are required usually 3 to about 5 hours.

The second step comprises acylating the free imine to form compound IV by treatment of III with an acyl halide such as tosyl chloride, benzenesulfonyl chloride, $C_{1-3}$ lower alkanoyl chloride, benzoyl chloride, or a $C_{1-3}$ lower alkyl chloroformate. Standard acylating conditions are employed such as contacting the two reagents in an inert organic solvent in the presence of an acid acceptor such as an organic base, especially pyridine, triethylamine, or an inorganic base, especially an alkali metal carbonate, or an alkaline resin, or the like. Reaction times and temperatures of 1 to 6 hours at about 0° C. to about 50° C. especially 2 to 4 hours at room temperature are employed.

The third step comprises the addition of an alkane across the imine double bond. Compound IV is treated with an alkyllithium in an inert organic solvent, especially an ether such as diethyl ether, tetrahydrofuran, 1,2-dimethoxyethane or the like at 0° C. to about 50° C., preferably room temperature for 0.5–4 hours, preferably about 1–3 hours.

The fourth step results in formation of the imine bridge by addition of the acylamino group across the conjugated double bond. The reaction is accomplished by treating the acylamino compound in an inert solvent such as a lower alkanol such as ethanol, propanol, butanol, or a chlorinated hydrocarbon such as chloroform or the like in the presence of an acid until the ring closure is complete. Reaction times of a few minutes to several days are employed depending on the structure of the particular starting material.

Temperatures from about 15° C. to about 150° C. or reflux temperatures can be employed. Where $R^1$ is other than hydrogen, the reaction proceeds readily at the lower temperatures. The acid can be a hydrogen halide or other anhydrous inorganic or organic acid such as trifluoroacetic acid, and where $R^1$ is other than hydrogen, chromatography of the starting material on silica gel with chloroform is sufficiently acidic to cause the cyclization.

Alternatively, the cyclization may be effected by treatment with a base such as an alkali metal hydroxide, especially sodium hydroxide in a hydroxylic solvent such as water or water/solvent mixtures such as aqueous dioxane, or an alkali metal alkoxide in a lower alkanol, especially a sodium lower alkoxide such as sodium methoxide in methanol at 50° C. to about 100° C.

The fifth and last step, formation of compound I, in which R is hydrogen, comprises deacylation of the imine group. These acyl groups are conveniently removed by acid or base hydrolysis at 25° to about 100° C. for 2 to 48 hours, preferably 6 to about 24 hours. In the case of the arylsulfonyl protective groups they are also removed by hydrogenolysis with an excess of sodium bis(2-methoxyethoxy)aluminum hydride in an inert organic solvent such as toluene at about 15° C. to about 50° C., preferably at 20° C. to about 30° C. for 6–48 hours, preferably about 12–24 hours.

If on the other hand the desired compound carries an alkyl group on the imine nitrogen, that is where R is alkyl or substitued alkyl, the compounds may be prepared by reduction of the N-alkanoyl compounds such as alkoxycarbonyl to give methyl or other alkanoyl groups to provide the other alkyl groups. The preferred reducing system is a metal hydride such as lithium aluminum hydride in an ethereal solvent such as ether, tetrahydrofuran or 1,2-dimethoxyethane or the like. The reaction proceeds satisfactorily at room temperature but temperatures from about 0° C. to about 50° C. are appropriate with reaction times of 10–13 hours.

An additional method of preparing those compounds wherein R is other than hydrogen involves the treatment of the unsubstituted imine with an aldehyde and sodium cyanoborohydride ($NaCNBH_3$) in an ether such as tetrahydrofuran, 1,2-dimethoxyethane or di(2-methoxyethyl)ether, preferably tetrahydrofuran, at about 10°–50° C., preferably 25° C., until the reaction is substantially complete, usually for about 6 hours to about 3 days, preferably about 2 days.

Where R is other than hydrogen, the compounds may also be prepared by alkylation of those compounds wherein R is hydrogen with the appropriate reagent of formula R-halo wherein halo represents chloro, bromo or iodo. The reaction is normally conducted in an inert solvent such as benzene, or toluene. However, the alkylating reagent, depending on its physical properties, may be used in sufficiently excess amount to act as solvent. It is preferred to conduct the reaction in the presence of an acid acceptor such as an inorganic carbonate such as sodium carbonate, an organic base such as pyridine, or a basic resin. Temperatures of about 50° C. to about 100° C. may be employed over reaction times of about 10 hours to about 5 days.

Compounds having a substituent on the benzenoid ring are generally prepared by metathesis of the appropriate bromo or iodo compound. For example treatment with an alkali metal lower alkoxide such as a sodium lower alkoxide in the presence of copper dust in a solvent such as dimethyl formamide at 50°–150° C. for 1–10 hours yields the corresponding lower alkoxy compound.

Similarly treatment of a bromo or iodo compound with cuprous cyanide in a solvent such as dimethyl formamide at reflux temperature for 1–10 hours yields the corresponding cyano compound.

Hydrolysis of the above cyano compounds with a mineral acid such as hydrochloric acid at reflux temperature produces the corresponding carboxy substituted compounds.

Also treatment of the bromo or iodo compounds with bis(trifluoromethylthio)mercury and copper dust or trifluoromethylthio-copper in a solvent such as dimethyl formamide or hexamethylphosphoric acid triamide at about 100°–200° C. for 1–10 hours yields the trifluoromethylthio derivatives.

The starting materials and processes used for preparing the intermediates used in the above described processes are fully described in the Examples.

Also included within the scope of the present invention are the non-toxic pharmaceutically acceptable salts of the novel compounds. Acid addition salts of the imine compounds are formed by mixing a solution of the imine with a solution of a pharmaceutically acceptable non-toxic acid such as hydrochloric acid, fumaric acid, maleic acid, succinic acid, acetic acid, citric acid, tartaric acid, phosphoric acid, or the like. Where the novel compound carries a carboxylic acid group, the invention also contemplates sodium, potassium, and calcium salts thereof.

The novel compounds can be resolved into their optical isomers by standard techniques, such as the formation of diastereomeric pairs by salt formation with an optically active acid, such as (−)di-p-toluoyl-d-tartaric acid and/or (+)-di-p-toluoyl-l-tartaric acid followed by fractional crystallization and regeneration of the free base.

In the method of treatment aspect of the present invention, the novel imines are capable of producing anxiety relief without causing excessive sedation or sleep at a dosage level of from about 0.01 to about 10 mg. per kilogram of body weight preferably about 0.5–5 mg/kg. of body weight on a regimen of 1–4 times a day. In addition, the novel compounds of the present invention are useful as muscle relaxants, anticonvulsants and in the treatment of extrapyramidal disorders when indicated at comparable dosage levels. It is understood that the exact treatment level will depend upon the case history of the animal or human individual being treated and in the last analysis the precise treatment level falling within the above guidelines is left to the discretion of the therapist.

Also included within the scope of the present invention are pharmaceutical compositions comprising the imines of this invention. Preferably these compositions are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, i.e., conventional tableting ingredients such as corn starch, lactose, sucrose, sorbitol, talc, stearic acid, magnesium stearate, dicalcium phosphate, gums, and other pharmaceutical diluents, e.g., water, to form a solid preformulation composition containing a homogeneous mixture of an imine of the present invention, or a non-toxic pharmaceutically acceptable salt, thereof. When referring to these preformulation compositions as homogeneous, it is meant that the active ingredient, is dispersed evenly throughout the composition so that the composition may be readily subdivided into equally effective unit dosage forms such as tablets, pills, capsules, and the like. This solid preformulation composition is then subdivided into unit dosage forms of the type described above containing from 0.1 to about 500 mg. of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like.

The liquid forms in which the novel composition of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, gelatin and the like.

EXAMPLE 1

6-Methylbenzo[5,6]cyclohepta[1,2-c]pyridin-11-one

Step A: Preparation of trans-4-(α-methylstyryl nicotinamide t-Butyl alcohol (29.6 g.) is added to a suspension of sodium hydride (12.6 g., 57% oil dispersion) in dimethylformamide (300 ml.) and the resulting mixture is warmed on the steam bath until hydrogen evolution ceases. The resulting stirred solution is cooled to 0° C. and a solution of 23.6 g. of 4-methylnicotinonitrile in dimethylformamide (100 ml.) is added dropwise (0.5–1 hour). The mixture is stirred at this temperature for an additional hour and a solution of acetophenone (24 g.) in dimethylformamide (100 ml.) is added dropwise. After 24 hours, the reaction mixture is poured over ice and the solution is acidified by the addition of glacial acetic acid. The solid that separates is filtered, washed with water and dried to give 38 g. of trans-4-(α-methylstyryl)nicotinamide, m.p. 150°–155°. Recrystallization from ethyl acetate produces product of m.p. 153.5°–155.5°.

Step B: Preparation of trans-4-(α-methylstyryl)-nicotinic acid

A mixture of trans-4-(α-methylstyryl)nicotinamide (5.1 g.), potassium hydroxide (5 g.), ethanol (50 ml.), and water (50 ml.) is heated under reflux for 24 hours. The ethanol is removed by distillation and the resulting aqueous solution is chilled and acidified by the addition of glacial acetic acid (5 ml.). The white solid that separates is filtered, washed with water, and dried to give 4.46 g. of trans-4-(α-methylstyryl)nicotinic acid, m.p. 151°–158° C. Recrystallization from ethanol followed by recrystallization from methanol gives material with m.p. 160°–161.5° C.

Step C: Preparation of 6-methylbenzo[5,6]cyclohepta-[1,2-c]pyridin-11-one

Trans-4-(α-methylstyryl)nicotinic acid (7.77 g.) is added to polyphosphoric acid with stirring (210° C.). The temperature of the stirred mixture is raised to 225° C. and maintained at 225°–230° C. for 0.25 hours. After cooling to 50° C. ice and water is added to 600 ml. total volume. The solution is made alkaline by the addition of concentrated aqueous ammonia and the solid that separates on cooling is filtered, washed with water, and dried to give 3.0 g. of 6-methylbenzo[5,6]cyclohepta[1,2-c]pyridin-11-one, m.p. 112°–116° C. Recrystallization from cyclohexane provides material with m.p. 117.5°–119.5° C.

Employing the procedure substantially as described in Example 1, Steps A, B, and C but optionally substituting for the acetophenone used in Step A thereof a corresponding molecular amount of a compound of structure

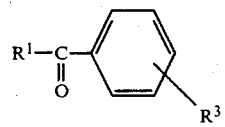

there are obtained the R[1]-benzocycloheptapyridinones described in Table I in accordance with the following reaction scheme:

TABLE I

| N | R[1] | R[3] |
|---|------|------|
| β | CH₃— | β'-Br |
| δ | n-C₃H₇— | β'-Br |
| δ | CH₂=CH—CH₂— | H |
| β | ⟨phenyl⟩—CH₂— | H |
| δ | ▷— (cyclopropyl) | β'-Br |
| β | ⟨cyclohexyl⟩— | H |
| δ | ⟨cyclohexyl⟩—CH₂— | β'-Br |
| β | ▷—CH₂— | H |
| β | C₂H₅— | β'-F |
| β | CH₃— | β'-F |
| β | H | β'-Br |
| β | H | β'-F |

EXAMPLE 2

5,6-Dihydro-6,11-dimethylbenzo[5,6]cyclohepta[1,2-c]pyridin-6,11-imine

Step A: Preparation of 11-imino-6-methylbenzo[5,6]cyclohepta[1,2-c]pyridine

Ammonia (gas) is bubbled into a chilled, stirred mixture of 6-methylbenzo[5,6]cyclohepta[1,2-c]pyridin-11-one (10 g., 0.048 mol), titanium tetrachloride (3.5 ml) and toluene (1000 ml) for 0.25 hours. The bath is removed and the resulting mixture is stirred at ambient temperature for four hours. Saturated sodium carbonate solution is added (1000 ml) and the mixture filtered to remove titanium salts. The layers are separated, the aqueous phase is extracted with ethyl acetate and the combined organic layers are washed with water, saturated aqueous sodium chloride solution, and dried over anhydrous sodium sulfate. The solvent is removed in vacuo, 6.5 g of 11-imino-6-methylbenzo[5,6]cyclohepta[1,2-c]pyridine, m.p. 165°-168° are obtained.

Step B: Preparation of 6-methyl-11-(p-toluenesulfonimino)benzo[5,6]cyclohepta[1,2-c]pyridine p-Toluenesulfonyl chloride (2.68 g, 0.014 mol) is added to a chilled stirred mixture of 11-imino-6-methylbenzo[5,6]cyclohepta[1,2-c]pyridine (2.6 g, 0.013 mol) and the cooling bath is removed. After 3 hours at 25°, the pyridine is removed in vacuo and the residue is recrystallized from EtOH to give 3.2 g, of 6-methyl-11-(p-toluenesulfonimino)benzo[5,6]cyclohepta[1,2-c]pyridine, m.p. 166°-168°.

Step C: Preparation of 6,11-dimethyl-11-(p-toluenesulfonamido)benzo[5,6]cyclohepta[1,2-c]pyridine Methyllithium (15 ml. 1.4 M in ether) is added to 6-methyl-11-(p-toluenesulfonimino)benzo[5,6]cyclohepta[1,2-c]pyridine (3.6 g, 0.01 mol) in tetrahydrofuran (25 ml). After two hours, the reaction mixture is diluted with 10% ammonium chloride solution and extracted with ethyl acetate. The extract is washed with water, saturated aqueous sodium chloride solution and dried over anhydrous sodium sulfate. Removal of the dried solvent in vacuo gives 3.0 g of 6,11-dimethyl-11-(p-toluenesulfonamido)benzo[5,6]cyclohepta[1,2-c]pyridine, m.p. 174°-177°.

Step D: Preparation of 5,6-dihydro-6,11-dimethyl-12-(p-toluenesulfonyl)benzo[5,6]cyclohepta[1,2-c]pyridin-6,11-imine A mixture of 6,11-dimethyl-11-(p-toluenesulfonamido)benzo[5,6]cyclohepta[1,2-c]pyridine (1.2 g), sodium hydroxide (24 g), water (24 ml) and dioxane (24 ml) is heated to reflux for 2 hours. The reaction mixture is cooled, diluted with water and extracted with ethyl acetate. The extracts are washed with water, saturated sodium chloride solution, and dried over anhydrous sodium sulfate. Removal of the solvent in vacuo produces 1.0 g of 5,6-dihydro-6,11-dimethyl-12-(p-toluenesulfonyl)benzo[5,6]cyclohepta[1,2-c]pyridin-6,11-imine, m.p. 199.5-201°.

Step E: Preparation of 5,6-dihydro-6,11-dimethylbenzo[5,6]cyclohepta[1,2-c]pyridin-6,11-imine fumarate A solution of 5,6-dihydro-6,11-dimethyl-12-(p-toluenesulfonyl)benzo[5,6]cyclohepta[1,2-c]pyridine-6,11-imine (1.0 g) in acetic acid (10 ml) and concentrated hydrochloric acid (5 ml) is heated to reflux for 24 hours. The cooled reaction mixture is diluted with water (150 ml), made alkaline by the addition of 20% sodium hydroxide solution, and extracted with ethyl acetate. The extracts are washed with water, saturated sodium chloride solution, and dried over anhydrous sodium sulfate. Removal of the solvent in vacuo and treatment of the residue with a boiling solution of fumaric acid in acetone gives 0.72 g of 5,6-dihydro-6,11-dimethylbenzo[5,6]cyclohepta[1,2-c]pyridin-6,11-imine fumarate.

Alternate Step E:

A solution of 5,6-dihydro-6,11-dimethyl-12-(p-toluenesulfonyl)benzo[5,6]cyclohepta[1,2-c]pyridin-6,11-imine (100 mg.) and 1 g. of a 70% (w/w) solution in benzene of sodium bis(2-methoxyethoxy)aluminum hydride in 15 ml. of toluene is stirred at room temperature for 24 hours. The mixture is poured into dilute caustic solution (2% w/v NaOH) and extracted with ethyl acetate. The ethyl acetate is concentrated to dryness and the residue is chromatographed over silica gel to give 5,6-dihydro-6,11-dimethylbenzo[5,6]cyclohepta[1,2-c]pyridin-6,11-imine which is converted to the fumarate as described above.

Following the procedure substantially as described in Example 2, but substituting for the benzo [5,6]cyclohepta[1,2-c]pyridin-11-one used in Step A, and the methyllithium used in Step C, the $R^1$-$R^3$-benzocycloheptapyridinones described in Table II there are produced the $R^1$-$R^2$-$R^3$-dihydrobenzocycloheptapyridinimines also described in Table II by the following process:

TABLE II

| N | $R^1$ | $R^3$ | $R^2$ |
|---|-------|-------|-------|
| β | CH₃— | β'-Br | CH₃— |
| δ | n-C₃H₇ | β'-Br | n-C₃H₇— |
| δ | CH₂=CH—CH₂— | H | ▱— |
| β | ⌬—CH₂— | H | C₂H₅— |
| δ | ▱— | β'-Br | CH₂=CHCH₂— |
| β | ⬡— | H | ⬡—CH₂— |
| δ | ⬡—CH₂— | β'-Br | ⬡— |
| β | ▱—CH₂— | H | CH₃— |
| β | C₂H₅— | β'-F | CH₃— |
| β | CH₃— | β'-F | ▱—CH₂— |
| β | H | β'-Br | CH₃— |
| β | H | H | CH₃— |

EXAMPLE 3

12-Allyl-5,6-dihydro-6,11-dimethylbenzo[5,6]cyclohepta[1,2-c]pyridin-6,11-imine

A mixture of 2.45 g. of 5,6-dihydro-6,11-dimethylbenzo[5,6]cyclohepta[1,2-c]pyridin-6,11-imine, 1.8 g of allyl bromide, 3.0 g of anhydrous sodium carbonate and 50 ml of dry toluene is heated at 80° C. for 20 hours. The mixture is filtered and the filtrate is evaporated in vacuo to give 12-allyl-5,6-dihydro-6,11-dimethylbenzo[5,6]cyclohepta[1,2-c]pyridin-6,11-imine which is converted to its hydrogen fumarate salt.

Employing the procedure substantially as described in Example 3, but using as starting materials the benzocycloheptapyridin-imines and the R-halides described in Table III, there are produced the R-benzocyclohepta-pyridin-imines also described in Table III in accordance with the following reaction:

TABLE III

| R | X | N | $R^2$ | $R^3$ | $R^1$ |
|---|---|---|-------|-------|-------|
| ⌬—CH₂ | Cl | β | —CH₃ | H | ▱—CH₂— |
| C₂H₅— | Br | β | —CH₃ | H | CH₃— |
| CH₂=CHCH₂— | Br | β | —CH₃ | β'-Br | CH₃— |
| C₂H₅— | Br | β | —C₂H₅ | H | ⌬—CH₂— |
| CH₃— | I | β | —CH₃ | H | H |
| ⬡— | Br | δ | n-C₃H₇ | β'-Br | n-C₃H₇— |
| ▱—CH₂— | Br | β | —CH₃ | H | ▱—CH₂— |
| (CH₃)₂NCH₂CH₂CH₂— | Br | δ | ▱— | H | CH₂CHCH₂— |
| CH₃— | I | β | —CH₃ | β'-Br | CH₃— |
| CH₃— | I | β | —CH₃ | H | CH₃— |

EXAMPLE 4

9-Methoxy-5,6-dihydro-6,11,12-trimethylbenzo[5,6]cyclohepta[1,2-c]pyridin-6,11-imine A mixture of 0.00905 mol. of 9-bromo-5,6-dihydro-6,11,12-trimethylbenzo[5,6]cyclohepta[1,2-c]pyridin-6,11-imine, 0.181 mole of sodium methoxide, 5.56 g. of electrolytic copper dust, and 87 ml. of dimethylformamide is stirred and heated on a steam bath for 2.5 hours. After cooling, 150 ml. of water and 150 ml. of ether is added to the mixture, and, after stirring, the mixture is filtered through a pad of diatomaceous earth. The ether phase is separated, washed with water, dried over magnesium sulfate, filtered, and the ether is removed on a rotary evaporator. The residue is dissolved in warm acetonitrile. On standing, the solution deposits crystals. The supernatant, containing the desired product, is decanted from the crystals. Evaporation of the solvent gives 9-methoxy-5,6-dihydro-6,11,12-trimethylbenzo[5,6]cyclohepta[1,2-c]pyridin-6,11-imine.

EXAMPLE 5

9-Cyano-5,6-dihydro-6,11-dimethylbenzo[5,6]cyclohepta[1,2-c]pyridin-6,11-imine

A mixture of 0.0249 mole of 9-bromo-5,6-dihydro-6,11-dimethylbenzo[5,6]cyclohepta[1,2-c]pyridin-6,11-imine, 4.58 gm. (0.0498 mole) of cuprous cyanide, and 30 ml. of dry dimethylformamide is stirred and heated under reflux for 6.5 hours. To the cooled solution (25° C.) is added 54 ml. of water, 27 ml. of a saturated aqueous solution of sodium cyanide, and 75 ml. of benzene. The mixture is stirred until a two phase system is obtained. The benzene phase is removed and the aqueous phase is extracted with two 75 ml. portions of benzene. The combined benzene phases are washed with 100 ml. of aqueous 0.1 M sodium cyanide, three 100 ml. portions of water, and dried over magnesium sulfate. After filtering, evaporation of the benzene gives a crystalline residue which is dissolved in the minimum volume of chloroform and passed over an alumina column (15″×1″)

packed in chloroform. The column is eluted with chloroform. Evaporation of the eluate provides 9-cyano-5,6-dihydro-6,11-dimethylbenzo[5,6]cyclohepta[1,2-c]pyridin-6,11-imine.

EXAMPLE 6

9-Carboxy-5,6-dihydro-6,11-dimethylbenzo[5,6]cyclohepta[1,2-c]pyridin-6,11-imine A mixture of 0.00318 ml. of 9-cyano-5,6-dihydro-6,11-dimethylbenzo[5,6]cyclohepta[1,2-c]pyridin-6,11-imine and 20 ml. of 6 N hydrochloric acid is stirred and refluxed for 18 hours. After cooling, the mixture is filtered, and the collected solid is washed with 6 N hydrochloric acid and then with ethanol and dried to give 9-carboxy-5,6-dihydro-6,11-dimethylbenzo[5,6]cyclohepta[1,2-c]pyridin-6,11-imine.

EXAMPLE 7

9-Trifluoromethylthio-5,6-dihydro-6,11-dimethylbenzo[5,6]cyclohepta[1,2-c]pyridin-6,11-imine A mixture of 2.24 g (0.0353 mol) of copper dust, 3.90 g (0.97 mol) of bis-(trifluoromethylthio)mercury, (0.00484 mol) of 9-bromo-5,6-dihydro-6,11-dimethylbenzo[5,6]cyclohepta[1,2-c]pyridin-6,11-imine and 20 ml of dimethylformamide is stirred and heated under reflux for six hours. The mixture is cooled in an ice bath and 100 ml of chloroform and 20 ml of concentrated ammonium hydroxide are added. The mixture is stirred overnight at room temperature and is filtered through a pad of diatomaceous earth. The filtrate and chloroform washings are combined and separated from the aqueous phase. The chloroform phase is washed with water, dried over magnesium sulfate, filtered, and the chloroform is removed on a rotary evaporator to give 9-trifluoromethylthio-5,6-dihydro-6,11-dimethylbenzo[5,6-]cyclohepta[1,2-c]pyridin-6,11-imine.

EXAMPLE 8

Preparation of intravenous solutions

A solution containing 10 mg. of 5,6-dihydro-6,11-dimethylbenzo[5,6]cyclohepta[1,2-c]pyridin-6,11-imine hydrogen fumarate per ml. of injectable solution is prepared in the following manner.

A mixture of 10 mg. of active ingredient and 9 mg. of sodium chloride is dissolved in sufficient water for injection to make 1 ml. of solution. The pH is adjusted using hydrochloric acid or aqueous sodium hydroxide to about pH 7.0.

If it is desired that the intravenous solution be used for multi-dose purposes, 1.0 mg. of methyl-p-hydroxybenzoate (methyl paraben) and 0.10 mg. of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.1, 1.0, 100.0 mg., respectively, of active ingredient per ml. of solution are similarly prepared substituting the indicated amount for the above-illustrated 10 mg. of quantity. Bulk injectable solutions of convenient volume for subsequent delivery in unit dosage form are readily prepared following the above procedure.

Following the above procedure, other representative injectable solutions of the present invention are prepared when the active ingredient used in 14 is replaced by an equivalent amount of any of the novel compounds of the present invention.

EXAMPLE 9

Tablet Preparation

Tablets containing 1.0, 2.0, 25.0, 26.0, 50.0, and 100.0 mg., respectively, of 5,6-dihydro-6,11-dimethylbenzo[5,6]cyclohepta[1,2-c]pyridin-6,11-imine are prepared as illustrated below.

| TABLE FOR DOSES CONTAINING FROM 1-25 MG. OF THE ACTIVE COMPOUND | | | |
|---|---|---|---|
| | Amount - mg. | | |
| 5,6-dihydro-6,11-dimethyl-benzo[5,6]cyclohepta[1,2-c]-pyridin-6,11-imine | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG. OF THE ACTIVE COMPOUND | | | |
|---|---|---|---|
| | Amount - mg. | | |
| 5,6-dihydro-6,11-dimethyl-benzo[5,6]cyclohepta[1,2-c]pyridin-6,11-imine | 26.0 | 50.0 | 100.0 |
| Microcrystalline cellulose | 25.0 | 100.0 | 200.0 |
| Modified food corn starch | 2.21 | 4.25 | 8.5 |
| Magnesium stearate | .39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg., 2.0 mg., 25.0 mg., 26.0 mg., 50.0 mg., and 100.0 mg. of active ingredient per tablet. Other tablets are prepared using the same procedures and the equivalent amounts of excipients along with equivalent amounts of any of the novel compounds of the present invention.

What is claimed is:

1. A process for the preparation of a compound of structural formula:

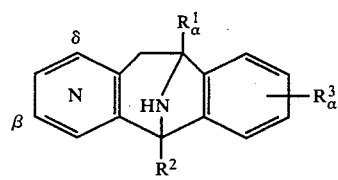

wherein N is in the $\beta$- or $\delta$-position; $R^2$ is
  (1) lower alkyl,
  (2) lower alkenyl,
  (3) phenyl-lower alkyl,
  (4) lower cycloalkyl, or
  (5) lower(cycloalkyl-alkyl);
$R_a^1$ is hydrogen or $R^2$,
$R_a^3$ is
  (1) hydrogen, or (2) halogen, which comprises the following steps, in sequence:

(a) treatment of a compound of formula:

[Structure: dibenzazepine-type tricyclic compound with N in left ring, $R_\alpha^1$ substituent, $R_\alpha^3$ substituent, and =O (ketone)]

wherein $R_\alpha^3$ is halo or hydrogen, with gaseous ammonia in the presence of titanium tetrachloride;

(b) treatment of the resulting imine of structure:

[Structure: tricyclic compound with $R_\alpha^1$, $R_\alpha^3$, and =NH]

with an acylating agent selected from tosyl chloride, benzenesulfonyl chloride, $C_{1-3}$ alkanoyl chloride, benzoyl chloride and a $C_{1-3}$ lower alkyl chloroformate in the presence of an acid acceptor;

(c) treatment of the resulting acylimine of structure:

[Structure: tricyclic compound with $R_\alpha^1$, $R_\alpha^3$, and =NAc]

wherein Ac is tosyl, benzenesulfonyl, $C_{1-3}$ alkanoyl, benzoyl, or $C_{1-3}$ alkoxycarbonyl, with an alkyl lithium of formula $R^2Li$:

(d) treatment of the resulting acylamine of structure:

[Structure: tricyclic compound with $R_\alpha^1$, $R_\alpha^3$, $R^2$, and NHAc substituents]

with an alkali metal hydroxide to produce the acylimine of structure:

[Structure: bridged tricyclic compound with Ac, $R_\alpha^1$, $R_\alpha^3$, $R^2$, and bridging N]

(e) treatment of the acylimine of Step (d) with a strong acid or strong base, or where Ac is an arylsulfonyl group with sodium bis(2-methoxyethoxy)aluminum hydride, to produce the imine of formula:

[Structure: bridged tricyclic compound with $R_\alpha^1$, $R_\alpha^3$, $R^2$, HN bridge]

2. The process of claim 1 for the preparation of the compound wherein N is in the β- position.

3. The process of claim 1 for the preparation of the compound wherein N is in the β- position, $R_\alpha^1$ and $R_\alpha^3$ are hydrogen and $R^2$ is loweralkyl.

4. The process of claim 1 for the preparation of the compound wherein N is in the β- position $R_\alpha^1$ and $R_\alpha^3$ are hydrogen and $R^2$ is methyl.

* * * * *